US00PP36582P3

(12) United States Plant Patent
Schoone

(10) Patent No.: US PP36,582 P3
(45) Date of Patent: Apr. 1, 2025

(54) ***PHALAENOPSIS* PLANT NAMED 'Body Language'**

(50) Latin Name: *Phalaenopsis hybrida*
Varietal Denomination: Body Language

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 18/735,094

(22) Filed: Jun. 5, 2024

(65) Prior Publication Data

US 2024/0415036 P1 Dec. 12, 2024

Related U.S. Application Data

(60) Provisional application No. 63/471,471, filed on Jun. 6, 2023.

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Phalaenopsis* plant named 'Body Language', characterized by its upright plant habit; moderately vigorous to vigorous growth habit; strong flowering stems; strong leaves; freely flowering habit with typically two inflorescences developing per plant, each inflorescence with numerous flowers; white-colored flowers with numerous purplish red-colored spots; and good post-production longevity.

2 Drawing Sheets

Figure 1:
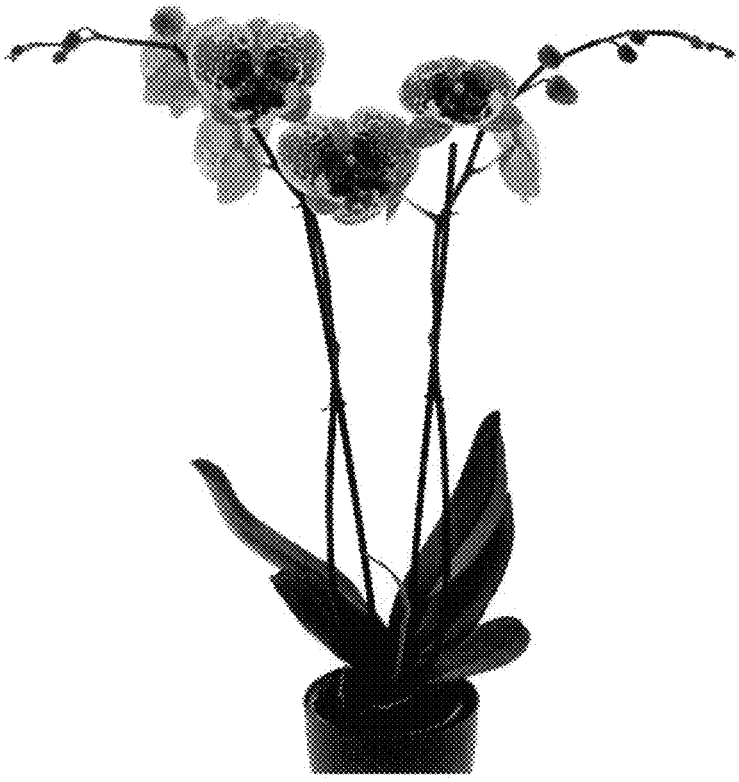

Botanical designation: *Phalaenopsis hybrida.*
Cultivar denomination: 'BODY LANGUAGE'.

STATEMENT REGARDING PRIOR DISCLOSURES BY INVENTOR AND APPLICANT/ASSIGNEE

A European Community Plant Breeder's Rights application for the instant plant was filed by the Applicant/Assignee of the instant application, Floricultura B.V. of Heemskerk, The Netherlands on Feb. 27, 2023, application number 2023/0511. Foreign priority is not claimed to this application.

The Inventor and Applicant/Assignee assert that no sales, offers for sale or public distribution of the instant plant occurred more than one year prior to the effective filing date of this application.

Any information about the claimed plant would have been obtained from a direct or indirect disclosure from the Inventor and/or Applicant/Assignee. Inventor and Applicant/Assignee claim a prior art exception under 35 U.S.C. 102 (b) (1) for disclosures and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida,* and hereinafter referred to by the name 'Body Language'.

The new *Phalaenopsis* plant is a product of a planned breeding program conducted by the Inventor in Assendelft and Heemskerk, The Netherlands. The objective of the breeding program is to develop new fast-growing and freely flowering *Phalaenopsis* plants with good leaf shape and flowers with unique and attractive patterns and coloration.

The new *Phalaenopsis* plant originated from a cross-pollination in May 2013 in Assendelft, The Netherlands of *Phalaenopsis hybrida* 'Tying Shin Eastern Star', not patented, as the female, or seed, parent with a proprietary selection of *Phalaenopsis hybrida* identified as code number 505031, not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in February 2020.

Asexual reproduction of the new *Phalaenopsis* plant by in vitro meristem propagation in a controlled environment in Assendelft, The Netherlands since March 2021 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Body Language'. These characteristics in combination distinguish 'Body Language' as a new and distinct *Phalaenopsis* plant:

1. Upright plant habit.
2. Moderately vigorous to vigorous growth habit.
3. Strong flowering stems.
4. Strong leaves.
5. Freely flowering habit with typically two inflorescences developing per plant, each inflorescence with numerous flowers.
6. White-colored flowers with numerous purplish red-colored spots.
7. Good postproduction longevity.

Plants of the new *Phalaenopsis* can be compared to plants of the female parent, 'Tying Shin Eastern Star'. Plants of the new *Phalaenopsis* differ primarily from plants of 'Tying Shin Eastern Star' in petal color as petals of plants of the new *Phalaenopsis* are white in color with numerous purplish red-colored spots whereas petals of plants of 'Tying Shin Eastern Star' are white in color but without spots. In addition, the cirrhose tips of plants of the new *Phalaenopsis* are shorter than the cirrhose tips of plants of 'Tying Shin Eastern Star'.

Plants of the new *Phalaenopsis* can be compared to plants of the male parent selection. Plants of the new *Phalaenopsis* differ primarily from plants of the male parent selection in flower color as flowers of plants of the new *Phalaenopsis* are white in color with numerous purplish red-colored spots whereas flowers of plants of the male parent selection are white in color with a moderate number of stripes. In addition, the central and lateral lobes of the labellum of the new *Phalaenopsis* are fused (forming what is called a "big lip") whereas the central and lateral lobes of the labellum of the male parent selection are not fused.

Plants of the new *Phalaenopsis* can be compared to plants of *Phalaenopsis hybrida* 'Beautiful Smile', not patented. In side-by-side comparisons, plants of the new *Phalaenopsis* differ primarily from plants of 'Beautiful Smile' in the following characteristics:

1. Flowers of plants of the new *Phalaenopsis* are broader than flowers of plants of 'Beautiful Smile'.
2. The central and lateral lobes of the labellum of the new *Phalaenopsis* are fused whereas the central and lateral lobes of the labellum of 'Beautiful Smile' are not fused.
3. Cirrhose tips of the labellum of plants of the new *Phalaenopsis* are white in color whereas cirrhose tips of the labellum of plants of 'Beautiful Smile' are purplish red in color with yellow-colored apices.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet FIG. 1 is a side perspective view of a typical flowering plant of 'Body Language' grown in a container.

Figure 2:
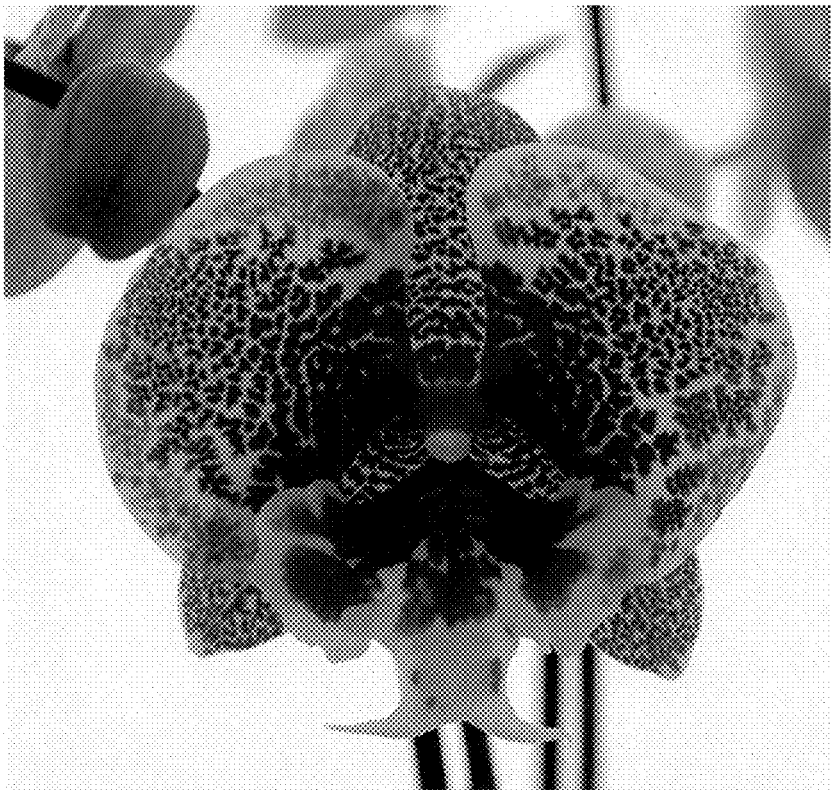

The photograph on the second sheet FIG. 2 is a close-up view of a typical flower of 'Body Language'.

DETAILED BOTANICAL DESCRIPTION

The aforementioned photographs and following observations and measurements describe plants grown during the late winter in 12-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27° C. During the final six months of production of the plants, day temperatures ranged from 20° C. to 22° C. and night temperatures ranged from 18° C. to 20° C. During the production of the plants, light levels ranged from a minimum of 5 klux to a maximum of 10 klux. In the following description, color references are made to The Royal Horticultural Society Colour Chart, 2015 Edition, except where general terms of ordinary dictionary significance are used.

Botanical classification: *Phalaenopsis hybrida* 'Body Language'.

Parentage:

*Female, or seed, parent.*—*Phalaenopsis hybrida* 'Tying Shin Eastern Star', not patented.

*Male, or pollen, parent.*—Proprietary selection of *Phalaenopsis hybrida* identified as code number 505031, not patented.

Propagation:

*Type.*—By in vitro meristem propagation.

*Time to initiate roots, summer and winter.*—About two weeks at temperatures about 28° C. to 30° C.

*Time to produce a rooted young plant, summer and winter.*—About 20 to 25 weeks at temperatures about 28° C. to 30° C.

*Root description.*—Thin, fibrous; typically light yellowish white in color; actual color of the roots is dependent on substrate composition, water quality, fertilizer, substrate temperature and age of roots.

*Rooting habit.*—Freely branching; medium density.

Plant description:

*Plant form and growth habit.*—Herbaceous epiphyte; upright plant habit with typically two inflorescences developing per plant, each inflorescence with numerous flowers; monopodial; moderately vigorous to vigorous growth habit and moderate growth rate.

*Plant height, substrate level to top of foliar plane.*—About 19.8 cm.

*Plant height, substrate level to top of floral plane.*—About 50.5 cm.

*Plant diameter or spread.*—About 37.9 cm.

Leaf description:

*Arrangement and quantity.*—Distichous, simple; sessile; about six fully-developed leaves per plant.

*Length.*—About 19.4 cm.

*Width.*—About 7.7 cm.

*Aspect.*—Semi-erect to somewhat outwardly arching.

*Shape.*—Obovate to oblong; slightly concave; slightly carinate.

*Apex.*—Unequal and broadly acute.

*Base.*—Sheathing. Sheath length: About 1.5 cm. Sheath width: About 1.5 cm. Sheath color, upper and lower surfaces: Close to 143B slightly tinged with close to 183A.

*Margin.*—Entire.

*Texture and luster, upper surface.*—Smooth, glabrous; slightly glossy.

*Texture and luster, lower surface.*—Smooth, glabrous; moderately glossy.

*Venation pattern.*—Camptodromous.

*Color*.—Developing leaves, upper surface: Close to 139A. Developing leaves, lower surface: Close to between NN137B and 146A slightly tinged with close to N186C. Fully expanded leaves, upper surface: Close to NN137A; venation, close to 143B. Fully expanded leaves, lower surface: Close to NN137B; venation, close to 146A.

Inflorescence description:

*Appearance and flowering habit*.—Showy zygomorphic flowers arranged on axillary simple or branched racemes; typically two inflorescences develop per plant; each inflorescence with about nine flowers; flowers face outwardly on outwardly arching inflorescences supported by upright peduncles; flowers with three petals, two lateral petals and one center petal transformed into a labellum and three sepals.

*Fragrance*.—None detected.

*Time to flower*.—Plants begin flowering about six months after planting; plants flower naturally during the winter into the spring.

*Flower longevity*.—Long flowering period, individual flowers maintain good substance for about ten weeks on the plant; flowers not persistent.

*Inflorescence length* (*lowermost flower to inflorescence apex*).—About 28.5 cm.

*Inflorescence width*.—About 15.6 cm.

*Flower buds, about two weeks before opening*.—Height: About 1.9 cm. Diameter: About 1.5 cm. Shape: Broadly ovate. Color: Close to 144B to 144C; towards the apex, slightly tinged with close to 182C.

*Flower size*.—About 9 cm (vertical) by 9.8 cm (horizontal).

*Flower depth*.—About 3.3 cm.

*Petals, quantity and arrangement*.—Three, two lateral petals and one center petal transformed into a labellum.

*Lateral petals*.—Length: About 4.7 cm. Width: About 6.2 cm. Shape: Roughly lunate to reniform. Apex: Rounded. Margin: Entire; not undulate. Texture and luster, upper surface: Smooth, glabrous; moderately velvety; matte. Texture and luster, lower surface: Smooth, glabrous; velvety; slightly glossy. Color: When opening, upper surface: Close to NN155D; towards the base, densely spotted, close to between 61A and 71A; towards the margins, less densely spotted, close to 72A to 72B. When opening, lower surface: Close to NN155D; distally, fine spots, close to 75A. Fully opened, upper surface: Close to NN155D; towards the base, densely spotted, close to between 71A and N79C; towards the margins, less densely spotted, close to N78B to N78D; colors do not change with subsequent development. Fully opened, lower surface: Close to NN155D; fine spots, close to 75A; colors do not change with subsequent development.

*Labella*.—Appearance: Three-parted with two lateral lobes and a central lobe; lobes fused forming a "big lip". Length, lateral lobes: About 2.9 cm. Width, lateral lobes: About 2.5 cm. Length, central lobe: About 4.5 cm. Width, central lobe: About 1.4 cm to 3.1 cm. Length, cirrhose tips: About 1.1 cm. Width, cirrhose tips, proximally: About 3.4 cm. Shape, lateral lobes: Flabellate. Shape, central lobe: Rhomboidal. Apex, lateral lobes: Obtuse. Apex, central lobe: Cleft with two backwardly curled cirrhose tips. Margins, lateral lobes: Irregularly dentate. Texture and luster, lateral and central lobes, upper and lower surfaces: Smooth, glabrous, moderately velvety; matte. Callosities: Located at the base of the labellum and attachment point of the lateral petals; about 3 mm in length, about 9 mm in width and about 6 mm in height. Color: When opening, upper surface: Lateral lobes: Close to NN155D; central blotch, close to N78A to N78B; proximally, close to 61A. Central lobe: Close to NN155D; irregular spots/blotches, close to 71A and N78A to N78B; towards the base, close to between 61A and 71A and at the base, close to 61A; cirrhose tips, close to NN155D. When opening, lower surface: Lateral lobes: Close to NN155D; central blotch, close to 76B. Central lobe: Close to NN155D; central blotch, close to N78C; at the base, close to 202D; main vein, close to 145D; cirrhose tips, close to NN155D. Fully opened, upper surface: Lateral lobes: Close to NN155D; central blotch, close to N78A to N78B; proximally, close to 61A. Central lobe: Close to NN155D; irregular spots/blotches, close to 71A and N78A to N78B; towards the base, close to between 61A and 71A and at the base, close to 61A; cirrhose tips, close to NN155D. Fully opened, lower surface: Lateral lobes: Close to NN155D; central blotch, close to 76C. Central lobe: Close to NN155D; central blotch, close to N78B to N78C; at the base, close to N155A; cirrhose tips, close to NN155D. Callosities, when developing and fully developed: Close to 10C with fine spots, close to 59B.

*Sepals*.—Quantity and arrangement: Three, one upper dorsal sepal and two lower lateral sepals. Length, dorsal sepal: About 5 cm. Width, dorsal sepal: About 3.3 cm. Length, lateral sepals: About 5.1 cm. Width, lateral sepals: About 3 cm. Shape, dorsal sepal: Roughly obovate. Shape, lateral sepals: Ovate. Apex, dorsal sepal: Obtuse. Apex, lateral sepals: Bluntly acute. Base, dorsal and lateral sepals: Cuneate. Margins, dorsal and lateral sepals: Entire; not undulate. Texture and luster, dorsal and lateral sepals, upper and lower surfaces: Smooth, glabrous; velvety; matte. Color, dorsal sepal: When opening, upper surface: Close to NN155D; densely blotched and spotted with close to 61A and towards the base, close to 72B. When opening, lower surface: Close to 145C; towards the apex and margins, close to 155C; fine spots, close to N75C to N75D. Fully opened, upper surface: Close to NN155D; densely blotched and spotted with close to N78A and towards the base, close to N78B and N78C. Fully opened, lower surface: Close to NN155C; fine spots, close to 76A to 76B. Color, lateral sepals: When opening, upper surface: Close to NN155C; towards the base, close to NN155A; densely blotched and spotted with close to 59A and towards the base, close to 70A, 70B and 72B. When opening, lower surface: Close to 145C; towards the apex and margins, close to 157C to 157D; fine spots, close to 182D. Fully opened, upper surface: Close to NN155D; densely blotched and spotted with close to 59A and 59B and towards the base, close to N78B and N78C. Fully opened, lower surface: Close to 145D; towards the apex and margins, close to NN155C; fine spots, close to 76A.

*Peduncles*.—Length: About 60 cm. Diameter: About 5 mm. Strength: Strong. Aspect: Upright to outwardly arching. Texture and luster: Smooth, glabrous; matte. Color: Close to between 147A and 202A covered with fine spots, close to 147B.

*Pedicels*.—Length: About 4.5 cm. Diameter: About 3 mm. Strength: Moderately strong. Aspect: About 60° from peduncle axis. Texture and luster: Smooth, glabrous; matte. Color: Close to N155B tinged with close to 76D; proximally, close to 144A.

*Reproductive organs*.—Androecium: Column length: About 9 mm. Column width: About 6 mm. Column color: Close to N78B; distally, close to NN155B. Pollinia quantity: Two. Pollinia diameter (per two pollinia): About 2.75 mm. Pollinia color: Close to 23A. Gynoecium: Stigma length: About 2 mm. Stigma width: About 4.5 mm. Stigma shape: Reniform. Stigma color: Close to N155A. Ovary length: About 8 mm. Ovary diameter: About 1 mm. Ovary color: Close to 150D. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'Body Language' as herein illustrated and described.

* * * * *